United States Patent [19]

Lilienfeld

[11] Patent Number: 5,349,844
[45] Date of Patent: Sep. 27, 1994

[54] SYSTEM AND METHOD FOR RESONANT FILTER MASS MONITORING

[75] Inventor: Pedro Lilienfeld, Lexington, Mass.

[73] Assignee: TRC Companies, Inc., Windsor, Conn.

[21] Appl. No.: 944,214

[22] Filed: Sep. 11, 1992

[51] Int. Cl.$^5$ .................. G01N 31/00; G01G 3/16
[52] U.S. Cl. .................. 73/28.01; 73/24.03; 177/210 FP
[58] Field of Search ........ 73/28.01, 28.05, 24.03, 73/24.06, 28.04; 177/210 FP; 422/73

[56] References Cited

U.S. PATENT DOCUMENTS

| | | | |
|---|---|---|---|
| 3,266,291 | 8/1966 | King, Jr. | 73/24.05 |
| 3,561,253 | 2/1971 | Dorman | 73/24.03 |
| 3,711,707 | 1/1973 | Lilienfeld et al. | 73/28.01 X |
| 3,744,297 | 7/1973 | Hanson et al. | 72/24.03 |
| 4,391,338 | 7/1983 | Patashnick et al. | 177/210 FP |
| 4,400,971 | 8/1983 | Tassicker | 73/28.01 |
| 4,827,760 | 5/1989 | Saito | 73/28.01 |
| 4,912,978 | 4/1990 | Solmos | 73/24.03 X |

FOREIGN PATENT DOCUMENTS 2203247A 10/1988 United Kingdom ............ 73/23.21

Primary Examiner—Robert J. Warden
Assistant Examiner—E. Leigh Dawson
Attorney, Agent, or Firm—Hale and Dorr

[57] ABSTRACT

A system and method for measuring particulate concentrations. The system includes a substantially planar, peripherally supported filter for capturing the particulates, an oscillator for oscillating the filter substantially perpendicular to its planar surface, and a sensor for measuring the frequency of oscillation.

28 Claims, 6 Drawing Sheets (0,0)
1.000

(1,0)
1.594

(2,0)
2.136

(0,1)
2.296

(3,0)
2.653

(1,1)
2.918

(4,0)
3.156

(2,1)
3.501

(0,2)
3.600

(5,0)
3.652

(3,1)
4.080

(6,0)
4.154

SYSTEM AND METHOD FOR RESONANT FILTER MASS MONITORING

TECHNICAL FIELD

The present invention relates generally to a system and method for measuring and monitoring the mass concentration of airborne particles.

BACKGROUND AND OBJECTS OF THE INVENTION

Over the past two decades, several techniques have been developed applicable to continuous direct reading monitoring of airborne particulate mass concentration. The relevant sensing techniques applicable to particulate monitoring are (a) beta radiation attenuation, (b) resonant frequency decrement, and (c) nephelometry.

1. Beta Radiation Attenuation

This technique has been incorporated in numerous experimental as well as commercial instruments in the U.S. and abroad. These devices typically fall into the following subcategories:
 (a) filter tape collectors
 (b) filter cartridge collectors, and
 (c) single-stage nozzle/plate impactors.

Each of the above radiation attenuation devices include a mass sensing stage, which is either separate from or combined with a particle collection stage. The mass sensing stage further includes a beta particle radiation source, typically carbon-14 or krypton-85, and a beta particle detector, typically a Geiger-Muller detector, plastic scintillator, or ionization chamber, which are placed on opposite sides of the collection substrate.

The attenuation of Beta electrons results from their interaction with the orbital electrons of the atoms in the path of the beta particle. The details of this process as it relates to aerosol particle monitoring may be found in the literature (Lilienfeld, P., Design and Operation of Dust Measuring Instrumentation Based on the Beta-Attenuation Method, Staub, Vol. 35, p. 458, 1975).

Specific characteristics of beta attenuation devices are as follows:

(a) mass measurement sensitivity increases when decreasing the collection area, when decreasing the emitted beta energy, and when increasing the total registered beta count;

(b) mass measurement errors arise from variations of the air density within the sensing gap during the period between the initial and final beta count cycles used to determine the mass increment. Further errors arise from sensitivity changes of the beta detector (e.g., temperature-related drift), particle collection inhomogeneities on the filter (or other substrate) area, the presence of elements whose ratio of atomic number to atomic mass deviates significantly from that of the elements used in the reference calibration, and changes of geometry between initial and final beta counting cycles (e.g., filter tape transport inaccuracies); and (c) additional factors contributing to measurement inaccuracies include intrinsic radioactivity of the collected sample, detector coincidence counting losses, as well as several other factors.

An important, albeit somewhat subjective, disadvantage of the beta attenuation technique is the negative perception associated with the use of a radioactive source which, although usually of low energy and low total activity (e.g., $E_{max}=150$ KeV for C-14 and 100 microcuries), nevertheless represents a perceived potential for radioactive contamination.

Lastly, the inherent sensitivity of the beta technique is marginal for short measurement periods (e.g., 30 minutes as with the present invention) unless extreme collection area concentrations are achieved, i.e., by means of nozzle/plate impaction. However, impaction entails additional particle collection drawbacks which would limit the device's usefulness in the context of the present invention.

2. Resonant Frequency Decrement

Any mechanical system including a mass in combination with a mechanical energy storage device (e.g., a spring) will tend to oscillate harmonically at its so-called natural resonance frequency, which is proportional to the square root of the ratio of the system stiffness constant and its mass. As this mass increases (e.g., by particle collection), the system resonant frequency decreases. This frequency decrement is a measure of the collected particle mass. There are a number of embodiments of this technique developed since the 1960's. The most important of these techniques are:

(a) oscillating wires or ribbons used as particle impaction surfaces (see Gast, T., Acoustical Feedback as Aid in the Determination of Dust Concentrations by Means of an Oscillating Ribbon, Staub, Vol., 30, p. 1, 1970 and Gast, T. and Bahner, H., Fortschritte bei der Messung yon Feststoffmengen mit Hilfe eines Schwingenden Bandes, Staub, Vol. 39, p. 109, 1979);

(b) quartz crystal piezo-balance (Olin, T. G., Sem, G. J. and Christenson, D. L., Piezo-Electrostatic Aerosol Mass Concentration Monitor, AIHR Jour., Vol. 209, 1971);

(c) tapered element oscillating mass monitor or TEOM (Patashnick, H. and Rupprecht, G., A New Real-Time Aerosol Mass Monitoring Instrument: the TEOM, Proceedings: Advances in Particle Sampling and Measurement, EPA-600/9-80-004, p. 264, 1980); and (d) oscillating filter tape monitor or MESA (Poss, G., Krann, U. and Solmos, A., A New Instrument for On-line Dust Monitoring, Aerosols: Formation and Reactivity, 2nd Int. Aerosol Conf. Berlin, p. 782, Pergamon Press, 1986).

Of the above techniques, methods (b) and (c) have received relatively broad use. The quartz crystal microbalance method combines either electrostatic precipitation (TSI, Inc.) to collect the particles on the surface of a quartz crystal (which is part of a resonant electronic circuit), or jet-to-plate impaction (e.g., California Measurements cascade piezo-balance impactor).

The principal advantage of the resonant mass monitoring technique, however, is that it represents the closest approximation to a reference gravimetric method, which cannot be used in many environments because gravimetric methods are not compatible with automated, continuous, indicating/recording of dust measurements. The resonant mass monitoring technique is, moreover, a direct mass sensing approach, as opposed to the other continuous sensing methods. It can be also considered as an absolute method in that the measured frequency decrement is predictably related to the increment of the collected particulate mass.

The principal disadvantages of the resonant technique are as follows:

(a) its inherent dependence on collected mass precludes discrimination against interference by liquid particles, especially water in the case of coal mines (a shortcoming shared with the beta attenuation technique);

(b) sensitivity to varying relative humidity, which is principally associated with filter material hygroscopicity; and (c) second or higher order effects affecting the stiffness constant of the resonating system.

These characteristic problems of resonant sensors will be addressed in detail in the subsequent section describing the central method proposed in the present invention: the resonant filter membrane mass monitor.

3. Nephelometry

Nephelometry is based on the measurement of the intensity of the light scattered by an ensemble of airborne particles, as opposed to single particle counting by light scattering. For an aerosol with a fixed size distribution of particles with invariant density and index of refraction, the intensity of light scattered within a given sensing configuration is directly proportional to the mass concentration of that aerosol (in the absence of multiple or of dependent scattering conditions which usually do not apply to the case under scrutiny). Although the effects of the particle size and index of refraction (on the relationship between light scattering vs. mass concentration) can be minimized for a given range of conditions, excessive deviations can not be avoided considering the entire range of aerosol parameters that may be encountered.

The principal advantages of nephelometry in this context are: a) superior sensitivity allowing true real-time measurements, b) relative simplicity of the sensing stage, c) compatible with miniaturization, ruggedization and long term maintenance free operation, and d) inherently independent of flow rate (except when used in conjunction with an active sampling system incorporating size selective inlet elements) allowing passive sampling which, in turn, minimizes power requirements and, consequently, overall weight.

It is important, however, to clarify that the above stated particle size and index of refraction limitations apply to monoparametric (i.e., basic intensity) nephelometry which in the present application is labelled as "dumb" nephelometry. By contrast, "smart" nephelometry, i.e. multiparameter nephelometry, can provide a far more complete characterization of an aerosol, virtually eliminating particle size and refractive index effects on mass measurements, and leaving only particle density as a "loose" parameter.

"Smart" nephelometry consists of the detection of light scattering as a function of one or more parameters that depend on particle size and index of refraction and—as no other real-time method can accomplish—particle shape. These parameters are: a) the phase function or scattering intensity as a function of scattering angle, b) wavelength dependence of the scattering and, in combination with the former, c) polarization/depolarization characterization. "Smart" nephelometry is especially useful as a means to detect and quantify the proportion of liquid water aerosol.

4. Summary of Background Art

Of the three salient techniques discussed in the background section, only the resonant oscillating method is strictly dependent upon mass and is the basis for the present invention. Heretofore, however, the resonant mass technique has suffered from a significant disadvantage: the need for either routine manual replacement of the particle collection medium (TEOM) or the requirement for elaborate and cumbersome collection surface restoration schemes (automated quartz crystal microbalance). In addition, devices such as the TEOM are susceptible to positional and vibrational effects which are of little or no consequence in well controlled stationary fixed point applications, but nevertheless become seriously limiting factors where these devices are to operate reliably within severe environments, e.g. blasting sites, coal mines, etc.

Other idiosyncrasies of TEOM-like devices are: the requirement for an inlet "chamber" from which the particle laden flow passes to the filter cartridge, i.e. this filter cannot be coupled directly to the system inlet (e.g. the cyclone exhaust port) because it must be allowed to oscillate freely, attached only to the tapered element. This inlet chamber has the potential for creating particle wall losses due to turbulent impaction, sedimentation and/or electrostatic forces.

Quartz crystal piezobalances exhibit other serious practical limitations that have constrained their application to largely laboratory uses. Principal among these problems are: exceedingly small total accumulated mass capacity of the quartz crystal (i.e. of the order of 100 $\mu g$) requiring very frequent crystal cleaning; and problems with particle adherence (vibrational coupling) to crystal, especially for particles larger than about 3 $\mu m$ and chain aggregates (such as combustion aerosols).

Other mechanical resonance schemes (some of which were mentioned in the background section) have proven impractical or insensitive: the taut wire or ribbon with transverse oscillation through excitation by capacitive means and particle collection by impaction investigated in the 1960's; the oscillating arm/pleated filter cartridge-spring-restored scheme developed at the General Electric Co. around 1970; and the more recent MESA system of Posh et al., incorporating an oscillating filter tape length with piezo-electric longitudinal excitation, applied to source emission monitoring (i.e. at concentrations of 10 to 1000 $mg/m^3$).

The above brief review demonstrates a long felt need for an improved sensing system and method which will accurately measure and monitor airborne particle concentrations.

It is an object of the present invention to provide a system and method for measuring and monitoring airborne particle concentrations.

Another object of the present invention is to provide a system and method for measuring and monitoring airborne particle concentrations in dusty environments which are potentially harmful to human health.

The foregoing specific objects and advantages of the present invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

Briefly described, the present invention consists of a system for accurately measuring the concentration of airborne particulates, particularly dust particles in potentially harmful environments. The system of the present invention preferably comprises a filter tape or disc for capturing airborne particulates, an oscillator for oscillating the filter medium, and a sensor for detecting the oscillations of the filter medium.

The mass of particulates collected on a taut filter is determined by oscillating that section of the filter (the collection area) to resonate at its natural mechanical resonant oscillation frequency. As particulates accumulate on the filter, the resonant frequency of the filtration medium's oscillation changes, decreasing due to the additional particulate mass.

The filter section is oscillated at its natural resonant frequency by an acoustical or electrical device, and the filter oscillations sensed by a microphone or other sensor. The particulate mass increment is determined from the change, i.e. decrease, in the natural resonant frequency. The mass concentration of airborne particulates is then computed.

According to one embodiment of the present invention, the system utilizes a single filter section.

According to another embodiment, the present invention utilizes two or more filter sections, which provide a sampling base measure for the mass concentration measurement.

Alternate embodiments of the present invention use one or more diametric and/or circular nodes on the filtration membrane.

It will be appreciated by those skilled in the art that the foregoing brief description and the following detailed description are exemplary and explanatory of the present invention, but are not intended to be restrictive thereof or limiting of the advantages which can be achieved by the invention. Thus, the accompanying drawings, referred to herein and constituting a part hereof, illustrate preferred embodiments of the invention and, together with the detailed description, serve to explain the principles of the invention.

BRIEF DESCRIPTION OF THE DRAWINGS

The invention will be more fully understood and other features and advantages thereof will become apparent from the description given below of exemplary embodiments of the invention, in which:

FIG. 3A illustrates an acoustic driver and laser beam detector, and FIG. 3B illustrates use of the filter membrane as a dielectric of a capacitor;

DETAILED DESCRIPTION OF THE PREFERRED EMBODIMENTS

Figure 1:
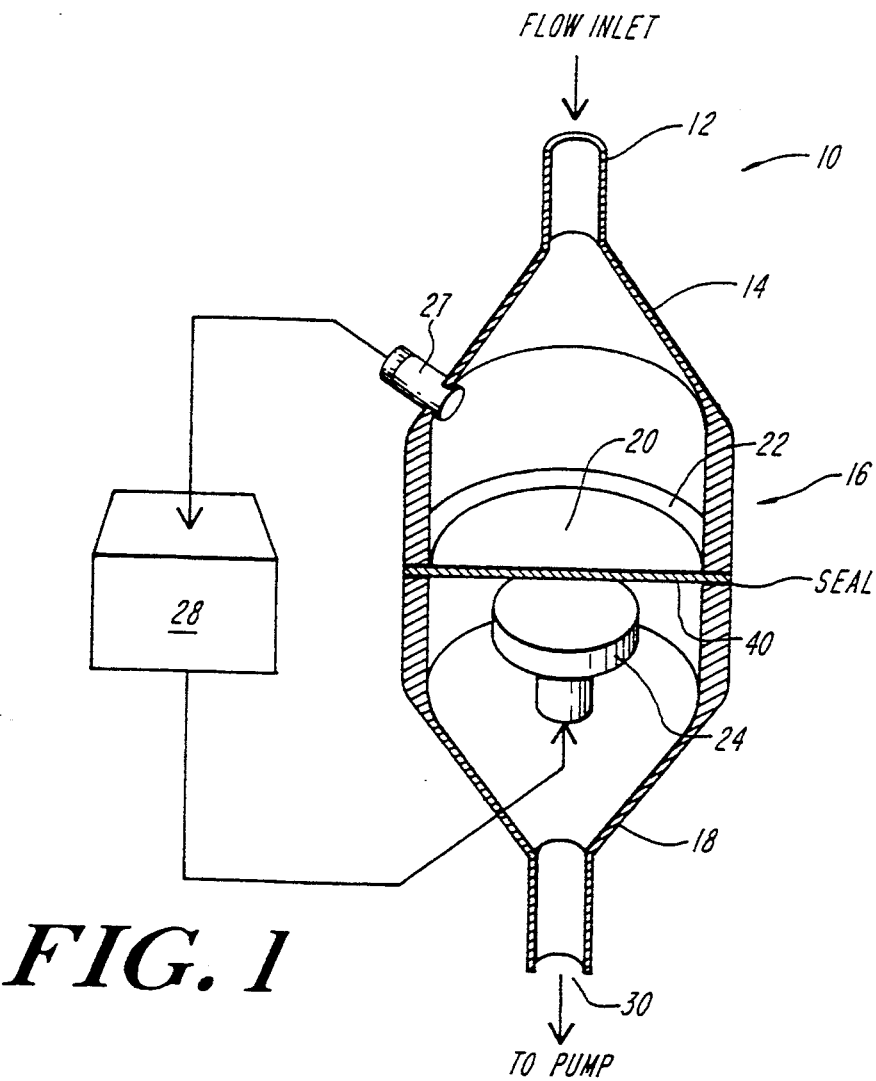
FIG. 1 is a cross-sectional view of the mass sensing system with a resonant filter/membrane.

Referring now to the accompanying drawings, wherein like reference characters refer to like parts throughout the various views, there are shown in FIGS. 1–7 the preferred embodiments of the resonant filter mass monitoring system according to the present invention.

FIG. 1 shows a general schematic view of the preferred mass sensing device 10 in accordance with the present invention. Shown in FIG. 1 is a sensing chamber 16 with an intake port 12 and an output port 30. An air sample is drawn from the ambient atmosphere by means of a pump (not shown).

Sensing chamber 16 is divided into an upper portion 14 and a lower portion 18. A filter membrane 20 separates both upper and lower chamber portions. Filter membrane 20 filters or collects any particulates present in the air sample flowing through intake port 12 into the upper portion 14 of sensing chamber 16. The air sample then flows through filter membrane 20, which collects particulates, and the air sample then flows out the output port 30. Sensing chamber 16 is preferably made of a rigid material (e.g. plastic or metal).

Filter membrane 20 may be made of any number of woven-type filter materials, preferably with a high degree of hydrophobicity to prevent the adsorption of environmental water "vapor, e.g., polyester, propylene, an acrylic polymer with a nylon substrate, or the materials sold under the trade names Teflon, Mylar, Gelman Versaped or". Versapor, Pallflex types TV20A45-TST, T070D and B057B, etc. Preferred materials show a high particle collection efficiency (over 95%) for all particle sizes to be monitored. Filter membrane 20 is preferably held taut within sensing chamber 16 by a peripheral ring 22, which preferably maintains the tautness of filter membrane 20 and which both connects and seals the upper 14 and lower 18 portions of the sensing chamber 16. Preferred filter membrane 20 materials also demonstrate appropriate mechanical resiliency and elasticity to provide a stable and repeatable resonant frequency, are chemically stable, and provide minimum flow resistance, i.e. pressure drop vs. face velocity.

Figure 2A:
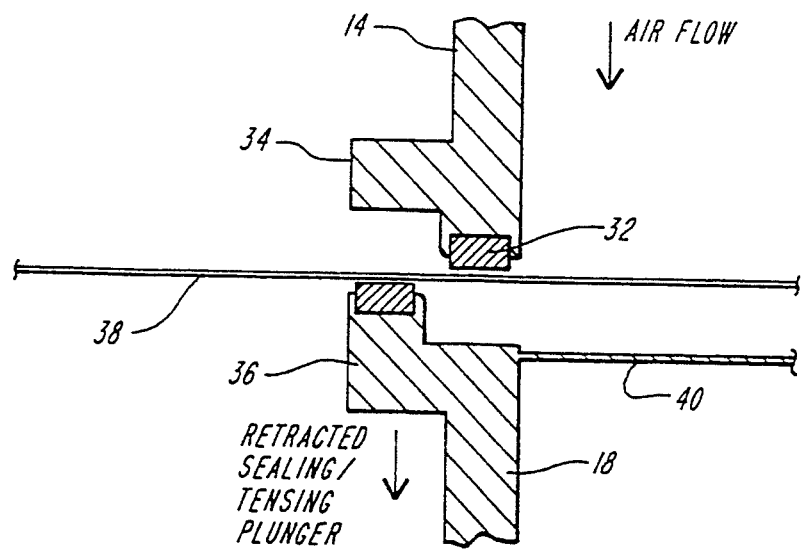
FIGS. 2A and 2B are cross-sectional views of the filter tape sealing/tensing elements for the plunger of the filter tape version.
Figure 2B:
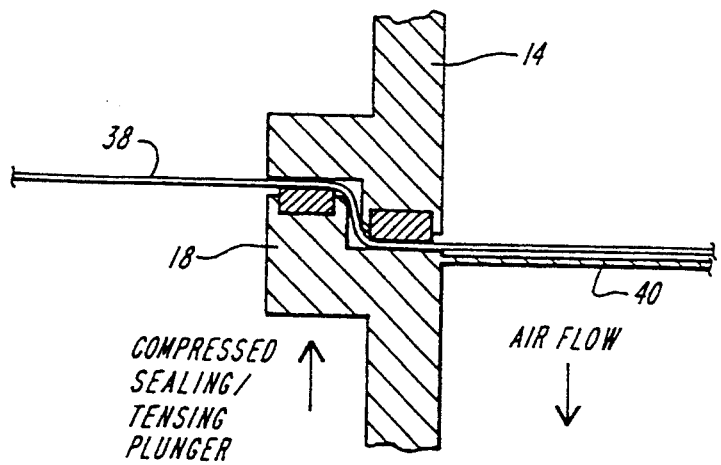

Filter membrane 20 may be held taut by peripheral ring 22 such as held in a filter cartridge as shown in FIG. 1, or may be sealed and tensed by means of a retractable plunger as shown in FIGS. 2A and 2B.

FIG. 2A shows the upper portion 14 and lower portion 18 of sensing chamber 16 retracted and separated. An L-shaped lip portion 34 is preferably formed along the edge of the upper portion 14 facing lower portion 18. A corresponding inverted L-shaped lip portion 36 is preferably formed along the edge of the lower portion 18 facing upper portion 14, as shown in FIG. 2A. Placed between the upper and lower portions of sensing chamber 16 is a filter tape 38 having a length and breadth adequate to cover the peripheral edge of the lip portions along the connection between the upper and lower portions of the sensing chamber 16.

Compression of the upper and lower portions both seals sensing chamber 16 and provides the requisite tension on filter membrane 20, as shown in FIG. 2B. Rubber gaskets 32 on the lip portions of the upper and lower chamber portions provide a further sealing and tensing function.

Also shown in FIGS. 1 and 2 is a back-up screen 40. Since the filter membrane 20 may become damaged by the passage of air, the "spring constant" of the membrane may become distorted, resulting in a change of resonant frequency and creating spurious readings. Back-up screen 40 may thus provide additional support to filter membrane 20 during flow conditions to resist permanent deformation. Alternatively, more resilient filter membrane materials may be employed. In any event, back-up screen 40 must be retracted during an acoustic sensing of the resonant frequency of filter membrane 20 in order to ensure freedom of oscillation to the filtration medium employed.

The preferred taut filter membrane configuration for use in portable personal monitors is circular. However, additional shapes, including ovals, triangles, squares, rectangles, and other polygons should be considered within the scope of the present invention. The preferred filter medium for mounted monitors, such as placed on heavy equipment or placed in a stationary position, is a filter in the form of a continuous tape having adequate width to cover the sensing area with a taut filter membrane.

In lower portion 18 of sensing chamber 16 below filter membrane 20 is a harmonic excitation driver 24, as shown in FIG. 1, which is either mechanically, electrically or acoustically coupled to filter membrane 20 in order to induce the oscillations of the taut membrane. There are several techniques available to oscillate filter membrane 20. The preferred direction of the generated oscillations are transverse, i.e. the motion is perpendicular to the plane of the membrane.

Mechanically induced oscillation of filter membrane 20 is obtained by a harmonic motion (perpendicular to the membrane plane) of the peripheral ring 22, e.g., by means of a piezoelectric driver.

Electrically induced oscillation of filter membrane 20 is obtained by application of an AC electric field, e.g. by means of a non-linear field where the filter membrane 20 acts as the dielectric of a capacitor (e.g., coplanar geometry). Also, a two-electrode configuration using a metallic filter may be employed.

Acoustically coupled harmonic oscillation of filter membrane 20 is obtained by use of a miniature sound generator (e.g., a high frequency sound transducer such as a small loudspeaker) across a small air gap.

Whichever excitation method is used to oscillate filter membrane 20 to its harmonic frequency, the frequency response or output is preferably essentially constant over the required frequency range (typically of the order of one octave) and is also preferably devoid of self-resonances (i.e. resonances of the exciter or driver) within that range of operation.

The taut filter membrane 20 is analogous to a miniature musical drum, and just as a drum exhibits characteristic resonant frequencies that depend, among other factors, on the mass of filter membrane 20. At the filter membrane's resonant frequency the amplitude of its oscillatory motion is at a marked maximum. Whereas the membrane's oscillation (induced by the harmonic drive 24) may be barely discernable at other frequencies, as the drive frequency sweeps through the resonance point, the intensity of the membrane oscillations increases sharply and are measurable.

Figure 3A:
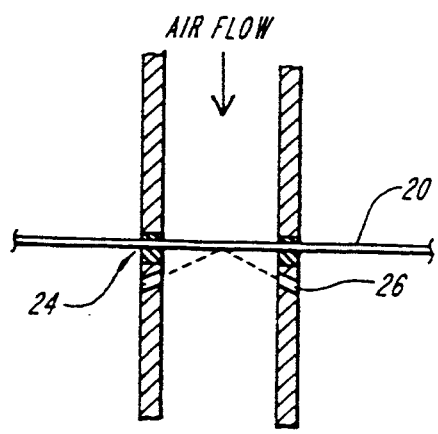
FIGS. 3A and 3B show ways to detect the resonant vibrations of the taut filter membrane.

Various methods may be used to detect the resonant vibrations of filter membrane 20 generated by excitation driver 24, including optical, capacitive, and acoustic. A preferred optical detector reflects a visible diode laser beam at a 45 degree angle from a source 25 to an optical motion pickup detector 26, as shown in FIG. 3A, wherein the oscillation frequency of the filter membrane 20 is sensed by the modulation of the detected light intensity.

Figure 3B:
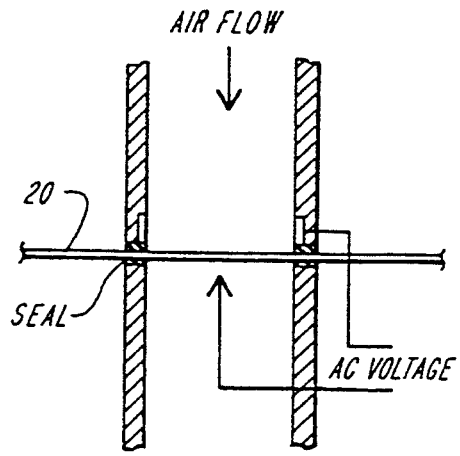
Figure 5A:
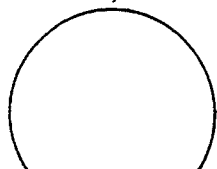
FIGS. 5A–5L show alternate configurations of filter membranes having diametric and/or circular nodes.
Figure 5B:
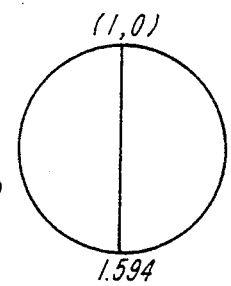
Figure 5C:
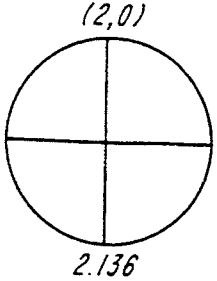
Figure 5D:
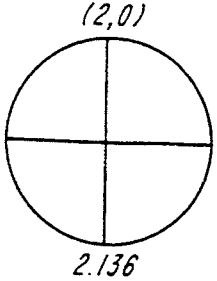
Figure 5E:
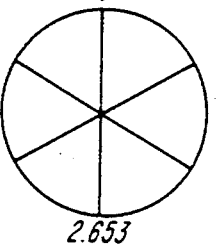
Figure 5F:
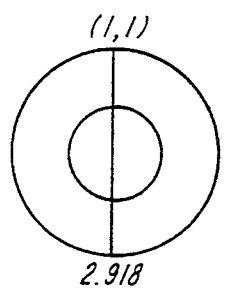
Figure 5G:
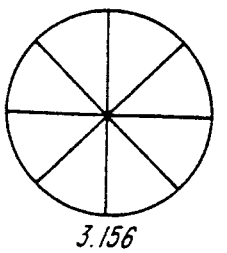
Figure 5H:
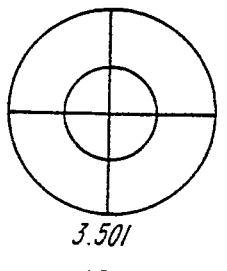
Figure 5I:
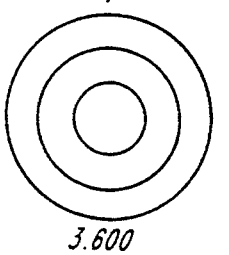
Figure 5J:
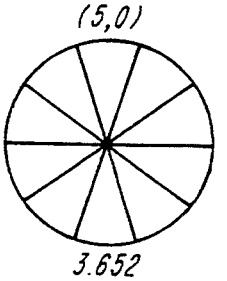
Figure 5K:
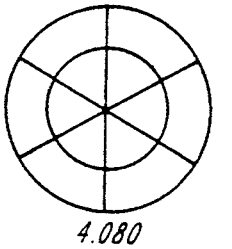
Figure 5L:
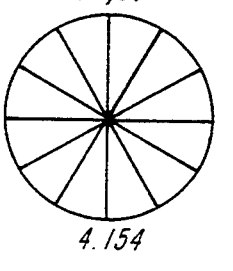

Capacitive detection methods involve using the filter membrane 20 as a dielectric of a capacitor (e.g., coplanar geometry), and sensing the frequency at which this capacitance undergoes a modulation maximum. As shown in FIG. 3B, application of an alternating current across the filter membrane 20 causes the membrane to vibrate.

Lastly, acoustic detectors detect the air pressure fluctuations associated with the reciprocating motion of the membrane which then acts as a secondary loudspeaker membrane. The resonant frequency is then detected by a microphone which is used to sense the oscillation frequency at which maximum intensity occurs.

Figure 4:
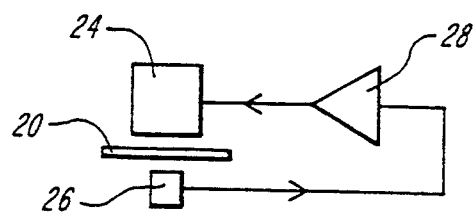
FIG. 4 shows a closed loop circuit having a feedback controlled oscillator to lock in at the harmonic frequency of the filter membrane.

The above detector methods not only sense the vibrations of the filter membrane 20, but preferably act with the harmonic driver 24, where both sensor and driver operate as a closed loop circuit through a variable frequency sinewave oscillator 28, as shown in FIG. 4. Feedback controlled oscillator 28 is thus designed to lock in at the frequency at which harmonic resonance of the filter membrane oscillation occurs. As dust particles or other particulates are collected on the filter membrane 20, its mass increases and, as a consequence, the filter membrane's resonant frequency decreases in a highly predictable manner.

A typical mass monitoring system, as shown in FIG. 1, uses a small piezo-electric transducer 24 that, for example, is acoustically coupled to the filter membrane 20 through a small air gap downstream of the filter in lower portion 18 of the sensing chamber 16. This configuration uses a taut filter membrane 20 supported within standard 37 mm or 25 mm plastic filter ring holders. The fundamental resonant frequency, in the range of 1000 Hz to 2000 Hz, was measured by means of an optical reflective pick up (or a small microphone may be employed). A coplanar capacitive excitation drive and pick up configuration may also be used, although the piezo-electric/acoustic drive is a straightforward and preferable technique. This piezo-electric transducer is preferably driven by a variable frequency oscillator 24 controlled by the feedback 28 from the electro-optical motion sensor, or microphone sensor 27. The frequency at which the oscillation amplitude of the filter membrane 20 is at a maximum is then maintained automatically, and this frequency is the sensed variable from which the accumulated mass is then computed. One of the significant advantages of the above approach is its small power demand and low voltage requirements, a characteristic that facilitates its intrinsic safety while also minimizing any electric fields that could affect particle collection on the oscillating filter (this latter aspect may be unimportant if the filter/membrane is excited only during short intervals rather than continuously).

The most salient advantage of the present sensing configuration is the fact that the collection surface and the resonant body are identical to each other, i.e. only the collection filter oscillates, thus minimizing the total resonating mass and maximizing sensitivity. Another important consequence is that such a minimal resonating mass is completely insensitive to positional changes due to shock and vibration, or any other externally applied mechanical stimulus (as opposed to the TEOM, as mentioned above). Additionally, this approach has a unique compatibility with automated collection substrate replacement when configured as a filter tape, a feature that is totally incompatible with resonant mass sensors such as the quartz piezo-balance and the TEOM.

Within subsequent sections the theory of taut circular membrane oscillation will be treated in the context of the present invention, and specific design details such as the filter medium criteria, excitation and pick up elements and associated electronic circuitry will be discussed.

3. Membrane Resonance Theory

The closed acousto-mechanical oscillating system of the present invention can be modeled by a combination of a mass-less stiffness and a stiffness-free mass. Such a system exhibits a fundamental resonant circular frequency $\omega_0$ given by the function:

$$\omega_0 = f(s,m)$$

where s is the stiffness or spring constant (force per unit distance) and m is the mass of the oscillating body.

Oscillating systems, such as strings, membranes, etc., however, are characterized by distributed masses and stiffnesses and thus exhibit several resonance frequencies (in the case of taut membranes these frequencies are not harmonically related, i.e. they are not integer multiples of the fundamental). For a taut circular membrane, the general expression for the characteristic resonant frequencies is:

$$\tilde{\omega}_{n,m} = k_{n,m} \sqrt{s'/m'} \quad (2)$$

where $\omega_{n,m}$ is the circular frequency as a function of the number of nodal circles, m, and the number of nodal diameters is n; $k_{n,m}$ are eigenvalues proportional to the Bessel functions of the first kind; and s' is the equivalent stiffness constant and m' is the equivalent mass, which are given by:

$$s' = F/R \quad (3)$$

$$m' = m/3 \quad (4)$$

where F is the uniform radial force exerted on the membrane (radial tension), R is the membrane total radius, and m is the membrane mass. Approximate values of $k_{n,m}$ of equation (2) are given in following table (Hütte, des Ingenieurs Taschenbuch, 28th edition, Vol. 1, p. 606ff, Wilhelm Ernst & Sohn, 1955):

| n/m | 0 | 1 | 2 | 3 |
|---|---|---|---|---|
| 0 | 1.00 | 2.30 | 3.60 | 4.90 |
| 1 | 1.59 | 2.92 | 4.23 | 5.54 |

The fundamental resonant frequency of a taut membrane $\omega_{0,0}$ is obtained when m=0 and n=0, i.e. $k_{n,m}$=1.00. Other resonances occur at higher frequencies given by the values of the above table. These other oscillation modes are associated with multiple circular and diametrical nodes (m>0 and or n>0). The following section further discusses the use of additional nodes in the present invention.

Returning to equation (2), if we replace equations (3) and (4) in that basic relationship, we obtain:

$$\tilde{\omega}_{n,m} = k_{n,m} \sqrt{3F/Rm} \quad (5)$$

which, for the fundamental frequency becomes:

$$\omega_{0,0} = \sqrt{3F/Rm} \quad (6)$$

Equation (6) indicates that the membrane resonant frequency depends upon the tension exerted at its periphery, the size of the membrane, and its total mass. It is this mass which increases as the dust is collected on the filter/membrane. Based on equation (6), the stability and precision of the accumulated mass measurement depends almost exclusively on the constancy of F, the radial tension of the membrane, and R which is an invariant dimensional constant of the system.

Assuming that the system is designed to seek the fundamental resonant circular frequency $\omega_{0,0}$, the initial frequency $f_0$, i.e., obtained before dust collection, will be given by:

$$f_0 = \frac{1}{2\pi} \sqrt{3F/Rm_0} \quad (7)$$

where $m_0$ is the tare or initial clean mass of the filter membrane 20. The final frequency $f_1$, i.e., after the dust has been collected, will thus be:

$$f_1 = \frac{1}{2\pi} \sqrt{3F/Rm_1} \quad (8)$$

where $m_1$ is the final mass of the filter (i.e. filter plus dust). The mass increment (i.e. the mass of the collected particulates) $\Delta m = m_1 - m_0$ can thus be obtained from the following simple relationship:

$$\Delta m = \frac{S}{4\pi^2} \left( \frac{1}{f_1^2} - \frac{1}{f_0^2} \right)$$

which is equivalent to:

$$\Delta m = m_0(f_0^2/f_1^2 - 1) \quad (9)$$

Consequently, based on equation (9), the mass concentration of particulates $C_m$ can be computed from:

$$C_m = \frac{s}{4\pi^2 Q t_s} \left( \frac{1}{f_1^2} - \frac{1}{f_0^2} \right)$$

which is equivalent to:

$$C_m = \frac{m_0}{Q t_s} (f_0^2/f_1^2 - 1) \quad (10)$$

where Q is the volumetric sampling flow rate and $t_s$ is the sampling time. For constant (regulated) flow rate and fixed time duration, and, assuming that $m_0$ is constant (i.e., within approximately 1% for a given filter type) from filter cartridge to cartridge (for the personal sampler), and from one filter spot to the next on the filter tape (for the machine mounted monitor), the measured variable is only the resonant frequency ($f_0$ at the beginning and $f_1$ at the end of a period). For a typical filter material such as Teflon, with a circular collection area in the practical range of 1 to 5 cm$^2$, the fundamental resonant frequency, $f_0$ will be of the order of 1,000 to 10,000 Hz (1 to 10 kHz).

4. Alternative Configurations

The circular filter taut membrane described above need not vibrate at the characteristic resonance frequency (the fundamental mode), but may instead oscillate at higher resonant modes for the measurement of accumulated mass. Operation at a higher resonance mode provides enhanced sensitivity and improved stability. FIGS. 5A–5L show the oscillation nodes of 12 resonant modes whose frequencies, as mentioned before, are not harmonically related. In the fundamental mode where $k_{n,m}=k_{0,0}=1.00$ and shown as (0,0) in FIG. 5A, the only nodal line (static line) is the circular periphery of the filter membrane 20. Oscillation at higher modes involves further diametrical and/or circular (concentric) nodes in addition to the peripheral node.

The number under each of the resonance diagrams of FIGS. 5A–5L is the factor by which the fundamental resonant frequency must be multiplied to obtain that particular modal frequency. For example, at the (0,1) mode (two concentric circular nodes) shown in FIG. 5D the resonant frequency is 2.296 times higher than at the fundamental frequency (0,0) in FIG. 5A (see Fletcher, N. H. and Rossing, T. D., The Physics of Musical Instruments, Springer Verlag, 1991). The mode shown in FIG. 5K (3,1) has one inner circular node in addition to the peripheral node, and three diametric nodes, and has a resonant frequency 4.060 times higher than the fundamental frequency. FIGS. 5A–5L are illustrative of some of the potential filter membrane configurations and modes for use in the present invention.

Figure 6:
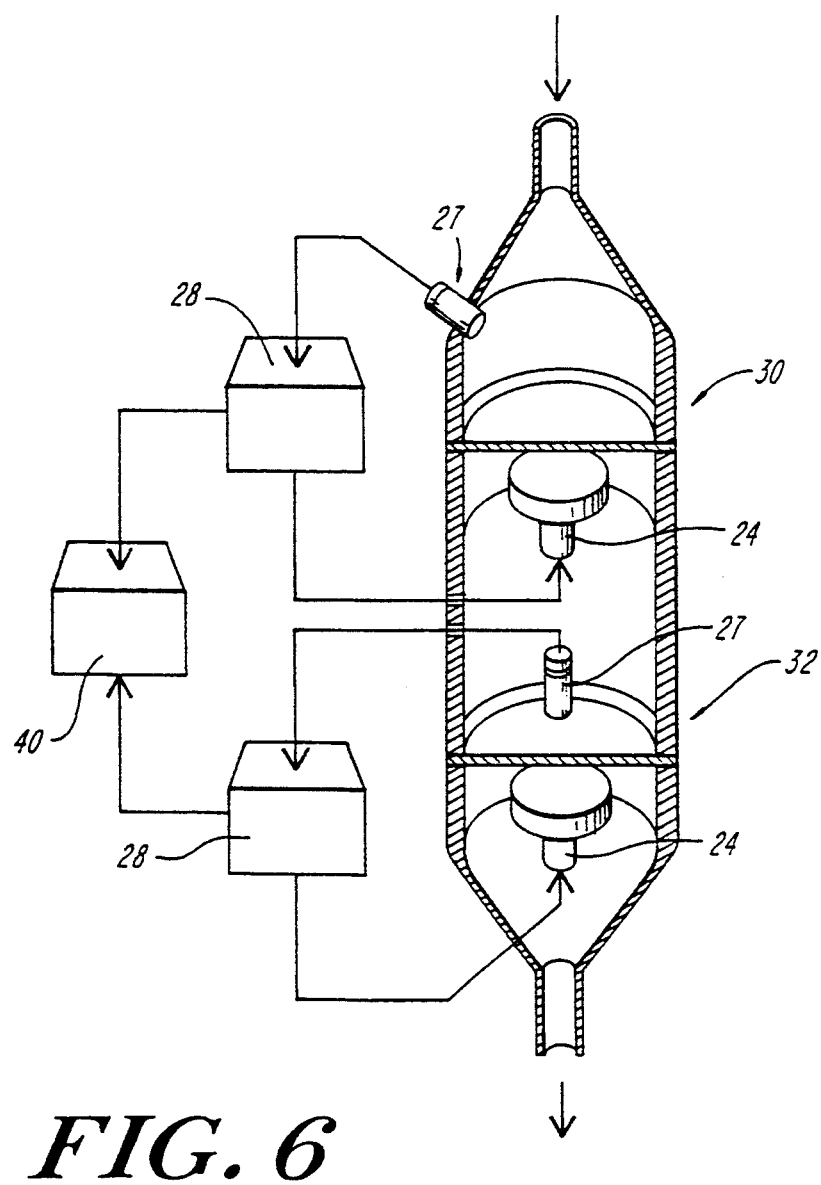
FIG. 6 is a cross-sectional view of an alternative two-stage sensing apparatus.
Figure 7A:
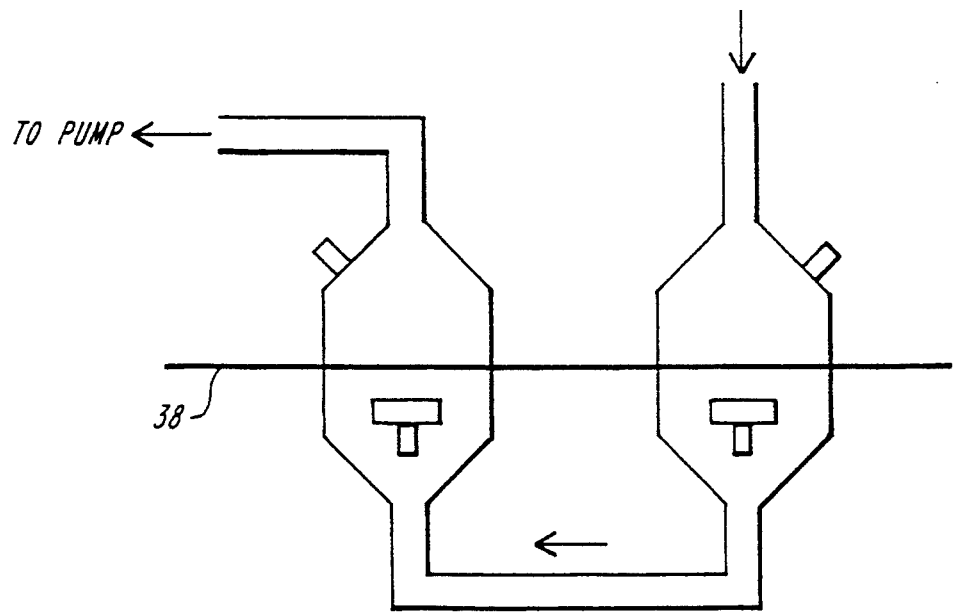
FIGS. 7A and 7B are cross-sectional views of other embodiments of a two-stage mass sensing monitoring devices.
Figure 7B:
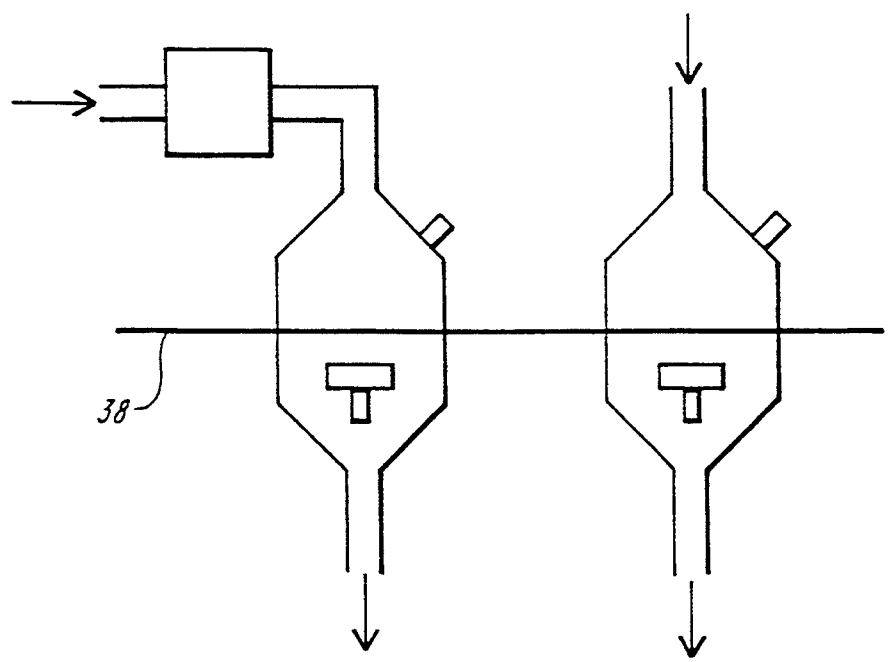

The entire preceding analysis applies to the simplest sensor configuration version, as shown in FIG. 1. A differential sensing method can also be applied to cancel out any spurious effects. This latter configuration, as shown in FIG. 6, consists of two consecutive identical sensing stages where the first sensing stage 30 (upstream) captures and senses the dust whereas the second (downstream) stage 32 serves as a reference. Any environmental factors affecting F, the filter/membrane tension, such as temperature, pressure, humidity, etc., would affect both stages equally, and would thus be canceled out by a frequency difference circuit 40, leaving only the dust mass increment on the first stage as the sensed variable. It should be emphasized, however, that the requirement for this two-stage sensing configuration is rather unlikely but the feasibility of its implementation provides a powerful "back up" solution. Mutual acoustic interference between sensing and reference stages (if it occurs) could be precluded by alternating operation (i.e., activating resonance of only one stage at a time).

In the case of a cartridge or cassette type monitor (e.g. personal monitor), the two-stage configuration consists of two identical filter membrane 20 cassettes and mass sensing stages connected in series as shown in FIG. 6. The reference sensing stage 32 is preferably a fixed part of the monitor, i.e., not requiring routine cassette replacement which would only be required for the upstream dust collection cassette. In the case of a continuous (filter tape) monitor, a similar series flow configuration may be employed with two adjacent filter tape stages (see FIG. 7a) as well as an alternative parallel flow approach (see FIG. 7b).

5. Experimental Confirmation of Technique

The theoretical basis of the present mass sensing method has been further confirmed by experiment. A thin Mylar membrane (simulating a filter membrane) was installed in a standard Millipore plastic filter holder whose rings served to maintain tautness. Two different sized holders were used: 25 and 37 mm diameter. Acoustic excitation was obtained from a small speaker placed at a distance of about 5 cm from one side of the taut membrane. Reflection of a visible diode laser beam illuminating at a 45 degree angle the opposite surface of the membrane was used to visually detect the frequency at which resonance occurred. The small speaker was driven by a sinewave generator whose frequency was manually varied. A digital frequency meter was then used to measure that frequency.

Figure 8:
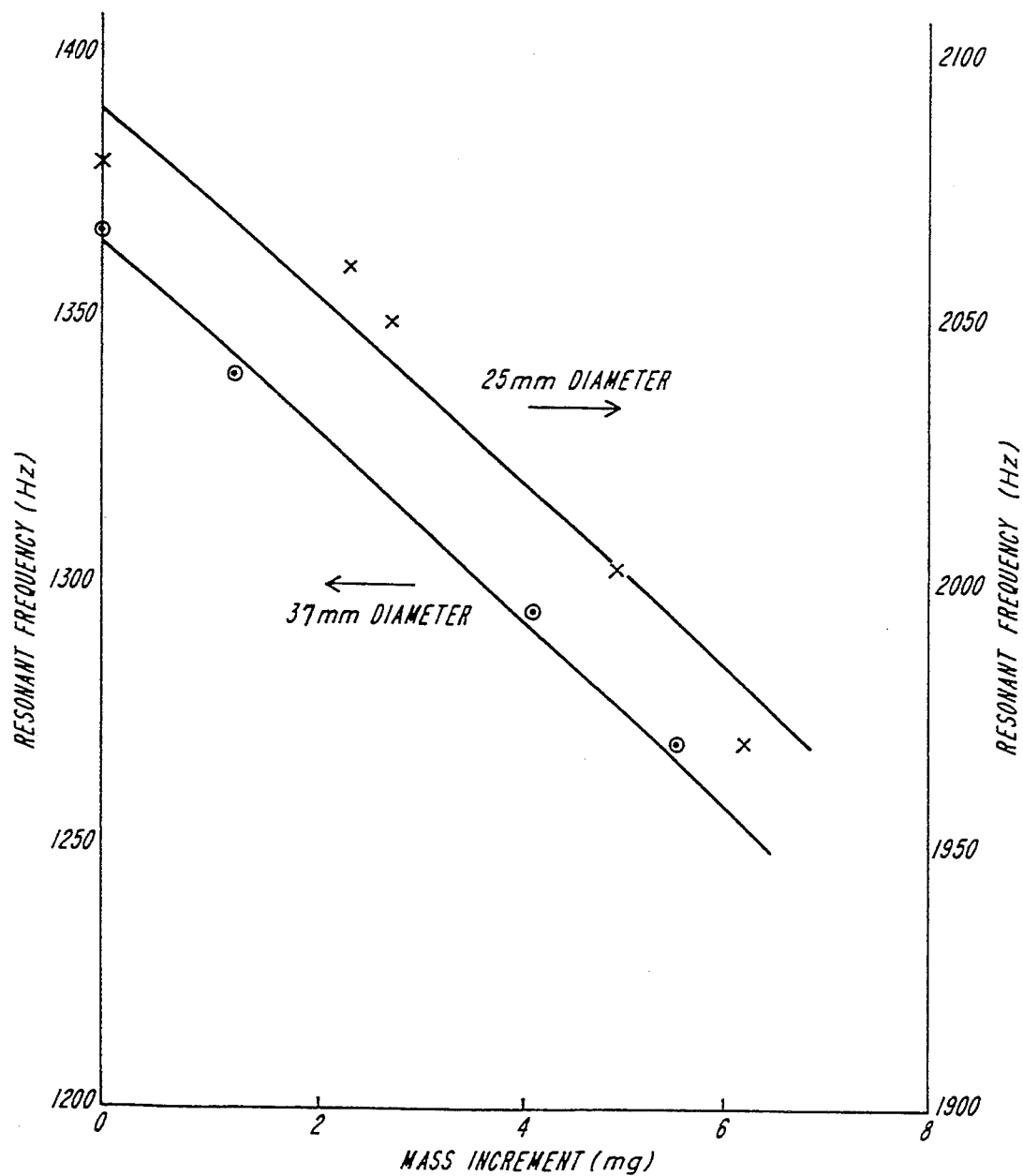
FIG. 8 is a chart plotting the fundamental resonant frequency as a function of mass increment for a taut membrane.

The plastic holder with its membrane was weighed on a precision balance to determine the initial weight and its increments. The weight (or mass) increments were applied to the membrane by spraying silicone oil from a pressurized aerosol dispenser, ensuring (by careful shielding) that only the membrane was being coated by the sprayed particles. After each spray application, the holder and membrane assembly was weighed and the membrane resonant frequency was then measured. FIG. 8 shows the results of these experiments. Different membrane tensions were used resulting in the nearly parallel lines of that graph. One of the important features that becomes obvious from the data of FIG. 8 is that the frequency decrement of $\Delta f = f_0 - f_1$ as a function of the mass increment $\Delta m$ is nearly independent of the membrane tension for the dimensions of this type of oscillating system, i.e. for the small increments under consideration, the ratio $\Delta f/\Delta m$ is nearly independent of other sensing parameters. It should be remembered that these other parameters (e.g. filter/membrane tension) are not expected to vary anyway.

The scatter of the data points of FIG. 8 was the inevitable result of the simplicity of the experimental procedures, dictated by time constraints; no attempts were made at controlling or maintaining membrane tension, the resonant condition was judged from the visual appearance of reflections, etc.

Although the experiment described above was rather crude and qualitative, its principal objectives were to: a) confirm the feasibility of sensing small mass increments by means of the filter/membrane resonant oscillation method, b) confirm the feasibility of harmonic excitation by simple means, i.e. using a small acoustic transducer behind the taut filter/membrane and c) perform the reliable detection of the resonant frequency (or frequencies). All of these objectives were achieved within the experiment, demonstrating unequivocally the feasibility and effectiveness of the present technique even when implemented in its simplest "breadboard" form.

While the invention has been described in connection with certain preferred embodiments, it will be understood that it is not intended to limit the invention to those particular embodiments. On the contrary, it is intended to cover all alternatives, modifications and equivalents as may be included in the appended claims. Some specific components, figures and types of materials are mentioned, but it is to be understood that such component values, dimensions and types of materials are, however, given as examples only and are not intended to limit the scope of this invention in any manner.

What is claimed:

1. A system for detecting airborne particulate concentration, comprising:
    (a) a substantially planar filter;
    (b) an air sampler for obtaining an ambient air sample and causing said air sample to flow through said filter whereby airborne particulates in said air sample are deposited on said filter;
    (c) an oscillator for causing oscillatory movement of said filter substantially perpendicular to the plane of said filter; and
    (d) a detector for detecting said oscillatory movement of said filter.

2. A system for detecting airborne particulate concentration according to claim 1, wherein said filter comprises a portion of a filter tape.

3. A system for detecting airborne particulate concentration according to claim 1, wherein said filter comprises a membrane.

4. A system for detecting airborne particulate concentration according to claim 1, wherein said filter comprises a circular membrane.

5. A system for detecting airborne particulate concentration according to claim 1, wherein said filter includes at least one diametric node.

6. A system for detecting airborne particulate concentration according to claim 1, wherein said filter includes a plurality of circular nodes.

7. A system for detecting airborne particulate concentration according to claim 1, wherein the periphery of said filter is attached to a fixed support.

8. A system for detecting airborne particulate concentration according to claim 1, wherein said filter is a membrane selected from the group consisting essentially of Teflon, polyester, polypropylene, and an acrylic copolymer with nylon substrate.

9. A system for detecting airborne particulate concentration according to claim 1, wherein said oscillator means comprises an acoustical drive.

10. A system for detecting airborne particulate concentration according to claim 9, wherein said acoustical drive comprises a piezo-electric harmonic drive.

11. A system for detecting airborne particulate concentration according to claim 1, wherein said oscillator means comprises a capacitive drive.

12. A system for detecting airborne particulate concentration according to claim 1, wherein said detector comprises a microphone.

13. A system for detecting airborne particulate concentration according to claim 1, wherein said detector comprises an optical motion pick-up device.

14. A system for detecting airborne particulate concentration according to claim 1, wherein said detector comprises a capacitive charge device.

15. A system for determining airborne particulate concentration, comprising:
    (a) a substantially planar filter;
    (b) an air sampler for obtaining an ambient air sample and causing said air sample to flow through said filter at a flow rate (Q) whereby airborne particulates in said air sample are deposited on said filter;
    (c) an oscillator for causing said filter to oscillate substantially perpendicular to the plane of said filter at a natural resonant frequency (f);
    (d) a detector for detecting said oscillatory movement of said filter; and
    (e) particulate concentration determining means for determining the airborne particulate concentration ($C_m$) of said sample based on the ratio between the initial ($f_0$) and final ($f_1$) resonant frequencies of said filter.

16. A system for determining airborne particulate concentration according to claim 15, wherein said concentration is obtained from said initial and final resonant frequencies of said filtration means.

17. A system for determining airborne particulate concentration according to claim 15, wherein said concentration of said sample is determined by equation:

$$C_m = \frac{s}{4\pi^2 Qt}\left(\frac{1}{f_1^2} - \frac{1}{f_0^2}\right)$$

where s is the filter stiffness, Q is the volumetric sampling flow rate, t is the elapsed sampling time period, and $f_0$ and $f_1$ are the initial and final resonant frequencies of said filter.

18. A system for determining airborne particulate concentration according to claim 15, wherein said elapsed sampling time period (t) is user selectable.

19. A system for determining airborne particulate concentration according to claim 15, wherein said airborne particulate concentration ($C_m$) is determined by equation:

$$C_m = \frac{m_0}{Qt}\left(\frac{f_0^2}{f_1^2} - 1\right)$$

where $m_0$ is the initial mass of the clean filter, Q is the volumetric sampling flow rate, t is the elapsed sampling time period, and $f_0$, $f_1$ are the initial and final resonant frequencies of said filter.

20. The system of claim 15 including a fixed support engaging and supporting the periphery of said filter.

21. A method for determining airborne particulate concentration, comprising the steps of:
    (a) obtaining an ambient air sample and providing said sample at a flow rate (Q);
    (b) collecting airborne particulates in said sample on a substantially planar filter;
    (c) oscillating said filter in a direction substantially perpendicular to the plane thereof;
    (d) detecting a natural resonant frequency (f) of said oscillating filter; and,
    (e) determining the airborne particulate concentration of said sample based on the ratio between initial ($f_0$) and final ($f_1$) resonant frequencies of said filter.

22. A method for determining airborne particulate concentration, according to claim 21, wherein said airborne particulate concentration of said sample is obtained from said initial and final resonant frequencies of said.

23. A method for determining airborne particulate concentration, according to claim 21, wherein said concentration of said sample is determined by equation:

$$C_m = \frac{s}{4\pi^2 Qt}\left(\frac{1}{f_1^2} - \frac{1}{f_0^2}\right)$$

where s is the filter stiffness, Q is the volumetric sampling flow rate, t is the elapsed sampling time period, and $f_0$ and $f_1$ are the initial and final resonant frequencies of said filter.

24. A method for determining airborne particulate concentration according to claim 20, wherein said airborne particulate concentration ($C_m$) is determined by equation:

$$C_m = \frac{m_0}{Qt}\left(\frac{f_0^2}{f_1^2} - 1\right)$$

where $m_0$ is the initial mass of the clean filter, Q is the volumetric sampling flow rate, t is the elapsed sampling time period, and $f_0$ and $f_1$ are the initial and final resonant frequencies of said filter.

25. The method of claim 21 wherein said filter is supported by a fixed peripheral support.

26. A system for determining airborne particulate concentration comprising a sampling chamber, a filter mounted within said chamber such that an air sample obtained by said chamber is passed through said filter and airborne particles in said sample are collected by said filter, an oscillator for oscillating said filter, and a detector for determining the concentration of particles collected by said filter, said system being characterized in that said filter includes a collection area on which said particles are collected, and said oscillator is arranged to oscillate substantially only the portion of said filter comprising said collection area.

27. The system of claim 26 further characterized in that said collection area is substantially planar.

28. The system of claim 27 further characterized in that said oscillator is arranged to oscillate said collection area in a direction substantially perpendicular to the plane thereof.

* * * * *